US010947826B2

(12) United States Patent
Kassab

(10) Patent No.: US 10,947,826 B2
(45) Date of Patent: Mar. 16, 2021

(54) STEAM INJECTION MONITORING, CONTROL AND OPTIMIZATION USING NEAR WELLHEAD SENSORS

(71) Applicant: GE Energy Oilfield Technology, Inc., Broussard, LA (US)

(72) Inventor: Amer M Kassab, Inverurie (GB)

(73) Assignee: GE Energy Oilfield Technology, Inc., Broussard, LA (US)

( * ) Notice: Subject to any disclaimer, the term of this patent is extended or adjusted under 35 U.S.C. 154(b) by 95 days.

(21) Appl. No.: 15/445,443

(22) Filed: Feb. 28, 2017

(65) Prior Publication Data

US 2017/0247991 A1 Aug. 31, 2017

Related U.S. Application Data

(60) Provisional application No. 62/301,512, filed on Feb. 29, 2016.

(51) Int. Cl.
| | |
|---|---|
| *E21B 43/24* | (2006.01) |
| *E21B 47/008* | (2012.01) |
| *E21B 33/068* | (2006.01) |
| *E21B 43/12* | (2006.01) |
| *G01N 33/00* | (2006.01) |

(52) U.S. Cl.
CPC ............ *E21B 43/24* (2013.01); *E21B 33/068* (2013.01); *E21B 43/128* (2013.01); *E21B 43/2408* (2013.01); *E21B 47/008* (2020.05); *G01N 33/0036* (2013.01)

(58) Field of Classification Search
CPC .. E21B 43/2406; E21B 43/2408; E21B 44/00; E21B 47/0007
See application file for complete search history.

(56) References Cited

U.S. PATENT DOCUMENTS

| | | | | |
|---|---|---|---|---|
| 4,488,598 A | * | 12/1984 | Duerksen | ................ E21B 43/12 |
| | | | | 166/252.4 |
| 4,938,174 A | * | 7/1990 | Bennett | ................ F22B 37/565 |
| | | | | 122/382 |

(Continued)

FOREIGN PATENT DOCUMENTS

| | | |
|---|---|---|
| RU | 2330950 C1 | 8/2008 |
| RU | 2555713 C1 | 7/2015 |
| WO | 03/062596 A1 | 7/2003 |

OTHER PUBLICATIONS

International Invitation to Pay Additional Fees issued in connection with corresponding PCT Application No. PCT/US2017/020042 dated Jul. 4, 2017.

(Continued)

*Primary Examiner* — Shane Bomar
(74) *Attorney, Agent, or Firm* — Crowe & Dunlevy, P.C.

(57) ABSTRACT

A steam-assisted hydrocarbon recovery system includes a wellbore, a wellhead connected to the wellbore, and a steam plant. The steam plant includes a steam generator, one or more steam lines connected between the steam generator and the wellhead, and a sensor module configured to measure a steam characteristic in the steam line near the wellhead. The steam-assisted hydrocarbon recovery system may also include an artificial lift system. Measurements made by the sensor module can be used to optimize the production of steam and the operation of the artificial lift system.

14 Claims, 1 Drawing Sheet

(56) References Cited

U.S. PATENT DOCUMENTS

| | | | | |
|---|---|---|---|---|
| 5,055,030 A * | 10/1991 | Schirmer | | E21B 36/003 |
| | | | | 122/31.1 |
| 5,085,275 A | 2/1992 | Gondouin | | |
| 6,978,741 B2 * | 12/2005 | Kemp | | F22B 37/565 |
| | | | | 122/447 |
| 8,097,128 B1 * | 1/2012 | Sherry | | B05B 1/308 |
| | | | | 203/11 |
| 9,777,562 B2 * | 10/2017 | Lastra | | E21B 43/12 |
| 2005/0224016 A1 * | 10/2005 | Kemp | | F22B 37/565 |
| | | | | 122/14.2 |
| 2006/0010865 A1 * | 1/2006 | Walker | | E21B 41/005 |
| | | | | 60/641.2 |
| 2009/0008088 A1 | 1/2009 | Schultz et al. | | |
| 2013/0175030 A1 | 7/2013 | Ige et al. | | |
| 2014/0166280 A1 * | 6/2014 | Stone | | E21B 43/12 |
| | | | | 166/268 |
| 2014/0284051 A1 | 9/2014 | Schneider et al. | | |
| 2014/0332218 A1 * | 11/2014 | Castrogiovanni | | E21B 43/24 |
| | | | | 166/302 |
| 2015/0198546 A1 * | 7/2015 | Wang | | G01N 25/60 |
| | | | | 702/24 |
| 2017/0074082 A1 * | 3/2017 | Palmer | | E21B 43/24 |
| 2017/0219203 A1 * | 8/2017 | Chandra | | E21B 43/24 |
| 2017/0234118 A1 * | 8/2017 | Part | | E21B 43/128 |
| | | | | 166/250.15 |
| 2019/0032913 A1 * | 1/2019 | Juranitch | | E21B 43/24 |

OTHER PUBLICATIONS

International Search Report and Written Opinion issued in connection with corresponding PCT Application No. PCT/US2017/020042, dated Oct. 5, 2017.

Russian Federal Service for Intellectual Property; May 6, 2020 Office Action for Russian Application 2018131102/03 (050595) based on PCT/US2017/020042 (with Google translation).

* cited by examiner

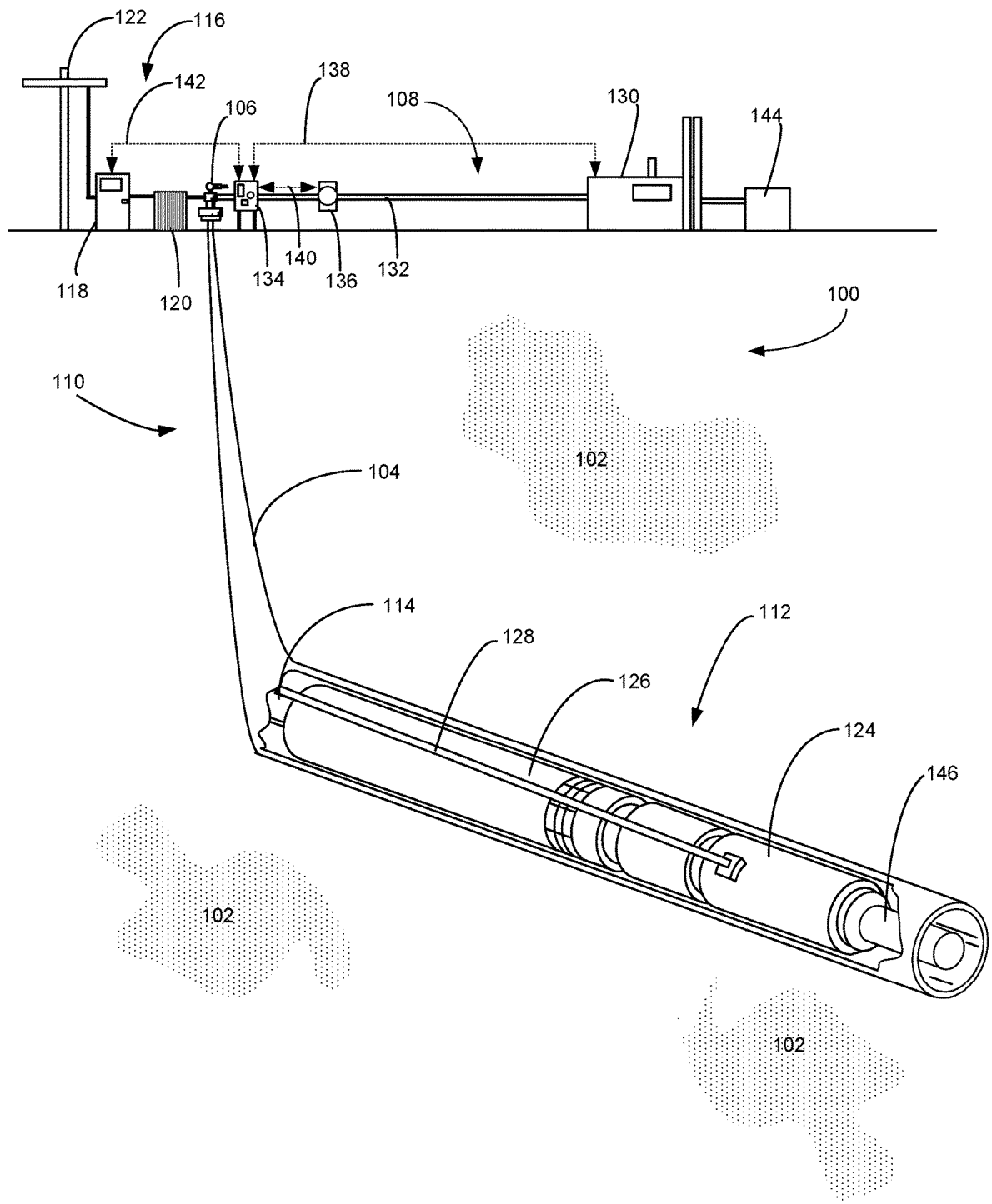

STEAM INJECTION MONITORING, CONTROL AND OPTIMIZATION USING NEAR WELLHEAD SENSORS

RELATED APPLICATIONS

This application claims the benefit of U.S. Provisional Patent Application Ser. No. 62/301,512 filed Feb. 29, 2016 entitled, "Steam Injection Monitoring, Control and Optimization Using Near-Well Head Sensors," the disclosure of which is herein incorporated by reference.

FIELD OF THE INVENTION

This invention relates generally to the production of hydrocarbons from a subterranean formation using steam-assisted recovery methods, and more particularly, but not by way of limitation, to an improved system and method for monitoring, controlling and optimizing the application of steam to the reservoir.

BACKGROUND

Steam has been used for many years to aid in the recovery of hydrocarbons from subterranean reservoirs. Steam is used in conjunction with several enhanced oil recovery (EOR) methods including steam-assisted gravity drainage (SAGD), steam flooding and cyclic steam stimulation (also known as "Huff and Puff"). In each case, the steam is useful in heating heavy oil and bitumen to reduce the viscosity of the hydrocarbons and improve the rates and amounts of recovery.

Steam is typically produced by a steam plant and delivered to the well through steam lines. Boilers and steam generators within the plant produce the steam at selected pressures and temperatures. Changes in the temperature and pressure of the steam may significantly impact the effectiveness of the recovery effort. Similarly, steam quality (steam dryness) (and steam purity) may also impact the steam injection operation. There is, therefore, a need to effectively monitor the characteristics of the steam used in oil recovery operations.

SUMMARY OF THE INVENTION

In an embodiment, the present invention includes a steam-assisted hydrocarbon recovery system for use in connection with a wellbore. The steam-assisted hydrocarbon recovery system includes a wellhead connected to the wellbore and a steam plant. The steam plant includes at least one steam generator, one or more steam lines connected between the steam generator and the wellhead and a near-wellhead sensor module configured to measure a steam characteristic in the steam line near the wellhead. The steam-assisted hydrocarbon recovery system may also include an artificial lift system that includes a downhole sensor module. Measurements made by the sensor modules can be used to optimize the production of steam and the operation of the artificial lift system.

BRIEF DESCRIPTION OF THE DRAWINGS

FIG. 1 is a perspective view of a steam-assisted hydrocarbon recovery system constructed in accordance with an exemplary embodiment.

WRITTEN DESCRIPTION

In accordance with exemplary embodiments of the present invention, FIG. 1 shows a perspective view of a steam assisted hydrocarbon recovery system 100. The system 100 is used to allow the production of hydrocarbons from a reservoir 102 through one or more wellbores 104 (a single wellbore 104 is shown in FIG. 1). The wellbore 104 includes a surface-mounted wellhead 106 that connects the wellbore 104 to downstream storage or refining facilities.

The steam assisted hydrocarbon recovery system 100 includes a steam plant 108 and an artificial lift system 110. In the embodiment depicted in FIG. 1, the artificial lift system 110 includes an electric submersible pumping system 112 attached to production tubing 114. The pumping system 112 and production tubing 114 are disposed within the wellbore 104. The production tubing 114 connects the pumping system 112 to the wellhead 106 located on the surface.

As used herein, the term "hydrocarbon" refers broadly to all mineral hydrocarbons, such as heavy crude oil, bitumen, gas and combinations of oil and gas. It will also be understood that, although the artificial lift system 110 of FIG. 1 is depicted in a deviated or non-vertical wellbore 104, the artificial lift system 110 and methods disclosed herein will find also utility in traditional vertical wellbores. Furthermore, although the artificial lift system 110 in FIG. 1 is the electric submersible pumping system 112, it will be appreciated that in other embodiments the artificial lift system 110 includes a different pumping mechanism. Alternative artificial lift systems 110 include surface-based sucker rod pumps, progressive capacity pump and plunger lift systems.

The artificial lift system 110 includes surface facilities 116 that control the pumping system 112. The surface facilities 116 can include a motor controller 118, a transformer 120 and a power source 122. The power source 122 includes one or both of a public electric utility and an independent electrical generator. Electricity is fed by the power source 122 to the motor controller 118. In some embodiments, the motor controller 118 is a variable speed drive (VSD) that is configured to control the operation of the pumping system 112 by adjusting the frequency or the speed provided to an electric motor 124 within the pumping system 112. When energized, the electric motor 124 drives a pump 126 that evacuates fluids from the wellbore 104 through the production tubing 114. Power is supplied to the motor 124 through a power cable 128.

The steam plant 108 includes a steam generator 130, steam lines 132, at least one near-wellhead sensor module 134 and a make-up water source 144. The steam plant 108 optionally includes a blowdown valve 136. The steam generator 130 includes a boiler or similar device that produces steam by heating water. The steam is carried from the steam generator 130 to the wellhead 106 through the steam lines 132. The steam generator 130 may be spaced apart from the wellhead(s) 106 by a significant distance. Although the steam lines 132 are shown above ground, it will be understood that the steam lines 132 may also be insulated and buried under the surface to reduce heat loss to the surrounding environment. The blowdown valve 136 can be used to purge dissolved solids and other accumulated impurities or condensate from the steam line at the wellhead 106.

Unlike prior art steam generation systems, the near-wellhead sensor module 134 of the system 100 is positioned near the wellhead 106. In some embodiments, the near-wellhead sensor module 134 is positioned within 50 meters of the wellhead 106. In other embodiments, the near-wellhead sensor module 134 is placed within 25 meters of the wellhead 106. The near-wellhead sensor module 134 includes one or more sensors configured to measure characteristics of the steam as it approaches the wellhead 106.

The near-wellhead sensor module 134 may be configured to measure the conductivity, temperature and optionally the pressure and pH of the steam flow. The total dissolved solids (TDS) value for the steam near the wellhead 106 can be derived from these measurements.

In one embodiment, the TDS of the steam is first measured at output of the steam generator 130 in the steam plant 108 or the inlet water of the generator. The steam is then reevaluated using the near-wellhead sensor module 134 near the wellhead 106. By measuring the TDS at the wellhead 106 and at the steam generator 130 output or input make up water 144, the injected steam quality can be estimated as:

$$\left(1 - \frac{TDS_{in}}{TDS_{WH}}\right) \cdot k$$

Where $TDS_{in}$ is the steam TDS measured at the steam generator make-up water source 144 and $TDS_{WH}$ is the TDS at the wellhead 106, k is s system specific variable related to the water treatment and/or enthalpy and/or pipe size.

or $$\left(\frac{TDS_{WH}}{TDS_{GO}}\right) \cdot k \cdot GOQ$$

where $TDS_{GO}$ is the TDS at the generator output, GOQ is the quality at the generator output Note that:

$$TDS = \acute{\kappa}\sigma$$

where $\sigma$ is the conductivity in uS/cm and $\acute{\kappa}$ is the conversion factor.

Quality can be measured either by a TDS, or conductivity probe submersed in the steam line or in a steam trap without any pressure or temperature reading. Thus, rather than relying on steam quality measurements made only at the remote steam generator 130, the near-wellhead sensor module 134 permits the evaluation of the steam in real time and in much closer proximity to the wellhead 106. This reduces measurement errors attributable to changes in the quality of steam between the steam generator 130 and the wellhead 106. The placement of the near-wellhead sensor module 134 near the wellhead 106 presents a significant advantage over the prior art.

In particular, the near-wellhead sensor module 134 can be used to optimize the production of steam and the operation of the artificial lift system 110. In an embodiment, the near-wellhead sensor module 134 is connected to the steam generator 130 through a first signal line 138. Information about the steam quality near the wellhead 106 is fed by the near-wellhead sensor module 134 in real time to the steam generator 130. Based on the information provided by the near-wellhead sensor module 134, the steam generator 130 can adjust the qualities of the steam leaving the steam generator 130. The steam generator 130 is configured to adjust the temperature, pressure and TDS of the steam based on feedback from the near-wellhead sensor module 134.

The operation of the blowdown valve 136 can be controlled using information produced by the near-wellhead sensor module 134. The near-wellhead sensor module 134 is connected to the blowdown valve 136 through a second signal line 140. The blowdown valve 136 can be automatically manipulated using measurements from the near-wellhead sensor module 134 to drain condensate liquid and solids from the steam line 132 to maintain the steam within a quality and differential pressure set point threshold. The control system enabled by the near-wellhead sensor module 134, the steam generator 130 and the blowdown valve 136 permits more precise matching of the steam quality to design specifications for the steam injection application.

In another embodiment, the near-wellhead sensor module 134 is connected to the motor controller 118 through a third signal line 142. It will be appreciated that in some embodiments the artificial lift system 110 includes a surface-based motor. The measurement of steam quality and other characteristics of the steam approaching the wellhead 106 can be fed forward to the motor controller 118 to permit the adjustment of the operation of the artificial lift system 110 in advance of the steam entering the wellbore 104. For example, based on the desired characteristics of the steam (e.g., quality, pressure and flow rate), measured deviations in the steam approaching the wellhead 106 from those targets, and measurements made within the wellbore 104 (downhole pressure, temperature, and target flow rate), the operation of the artificial lift system 110 can be automatically adjusted according to pre-programmed algorithms to optimize the efficiency and rate of production of hydrocarbons from the reservoir 102.

In yet another embodiment, the pumping system 112 includes a downhole sensor module 146 that is configured to detect characteristics of the wellbore 104 near the pumping system 112. In particular, the downhole sensor module 146 is configured to measure the temperature and pressure of steam present in the wellbore 104 near the pumping system 112. By comparing these downhole temperature and pressure measurements against the temperature and pressure measurements made by the near-wellhead sensor module 134, a determination can be made regarding the extent to which the quality of steam has changed as it travels from the wellhead 106 to the downhole pumping system 112. Because steam-assisted recovery operations are modeled on a theoretical or predicted steam quality in the wellbore 104, the determination of any deviations from the intended design characteristics of the steam in the wellbore 104 enables the operator to adjust the operating parameters used to produce the steam at the steam plant 108 so that it more closely matches the design criteria in the wellbore 104.

It is to be understood that even though numerous characteristics and advantages of various embodiments of the present invention have been set forth in the foregoing description, together with details of the structure and functions of various embodiments of the invention, this disclosure is illustrative only, and changes may be made in detail, especially in matters of structure and arrangement of parts and steps within the principles of the present invention to the full extent indicated by the broad general meaning of the terms in which the appended claims are expressed. It will be appreciated by those skilled in the art that the teachings of the present invention can be applied to other systems without departing from the scope and spirit of the present invention.

What is claimed is:

1. A steam-assisted hydrocarbon recovery system for use in recovering hydrocarbons through a wellbore, the steam-assisted hydrocarbon recovery system comprising:
   a wellhead connected to the wellbore; and
   a steam plant, wherein the steam plant comprises:
      a steam generator;
      one or more steam lines connected between the steam generator and the wellhead; and a sensor module configured to measure a steam characteristic in the steam line near the wellhead, wherein the sensor module produces an output signal that is representative of the steam characteristic measured by the sensor module and wherein the output signal is used to adjust the operation of the steam generator; and an artificial lift system, wherein the artificial lift system comprises:
a submersible pumping system that includes an electric motor located in the wellbore; and
wherein the output signal is used to adjust the operation of the electric motor of the submersible pumping system.

2. The steam-assisted hydrocarbon recovery system of claim 1, wherein the steam generator includes a blowdown valve and wherein the output signal is used to adjust the operation of the blowdown valve to adjust the characteristics of the steam within the one or more steam lines.

3. The steam-assisted hydrocarbon recovery system of claim 1, wherein the steam characteristic is steam quality.

4. The steam-assisted hydrocarbon recovery system of claim 3, wherein the sensor module comprises a sensor configured to measure the total dissolved solids (TDS) of the steam.

5. The steam-assisted hydrocarbon recovery system of claim 1, wherein the steam characteristic is steam quality.

6. A steam-assisted hydrocarbon recovery system for use in recovering hydrocarbons through a wellbore with steam according to predicted qualities of the steam in the wellbore, the steam-assisted hydrocarbon recovery system comprising:
a wellhead connected to the wellbore;
a steam plant, wherein the steam plant comprises:
a steam generator;
one or more steam lines connected between the steam generator and the wellhead; and
a sensor module configured to measure a steam characteristic in the steam line near the wellhead, wherein the sensor module produces an output signal that is representative of the steam characteristic measured by the sensor module, and wherein the output signal is used to adjust the operation of the steam generator; and
a submersible pumping system that includes an electric motor and a pump driven by the electric motor, wherein the pump and the electric motor are located in the wellbore, and wherein the operation of the submersible pumping system is automatically adjusted in response to the output signal.

7. The steam-assisted hydrocarbon recovery system of claim 6, wherein the steam characteristic is steam quality.

8. The steam-assisted hydrocarbon recovery system of claim 6, wherein the sensor module is positioned within 50 meters of the wellhead.

9. The steam-assisted hydrocarbon recovery system of claim 6, wherein the system includes a blowdown valve and wherein the output signal is used to adjust the operation of the blowdown valve to adjust the characteristics of the injected steam within the one or more steam lines.

10. A steam-assisted hydrocarbon recovery system for use in recovering hydrocarbons through a wellbore, the steam-assisted hydrocarbon recovery system comprising:
a wellhead connected to the wellbore;
an artificial lift system that includes a downhole pumping system, wherein the downhole pumping system includes a downhole sensor module configured to measure steam characteristics in the wellbore and produce a first output signal that is representative of the steam characteristics measured by the downhole sensor module; and
a steam plant, wherein the steam plant comprises:
a near-wellhead sensor module configured to measure a steam characteristic near the wellhead, wherein the sensor module produces a second output signal that is representative of the steam characteristic measured by the near-wellhead sensor module; and
a steam generator, wherein the operation of the steam generator is automatically adjusted in response to the first output signal and the second output signal.

11. The steam-assisted hydrocarbon recovery system of claim 10, wherein the operation of the artificial lift system is automatically adjusted in response to the first output signal and the second output signal.

12. The steam-assisted hydrocarbon recovery system of claim 10, wherein the system includes a blowdown valve and wherein the second output signal is used to adjust the operation of the blowdown valve to adjust the characteristics of the injected steam within the one or more steam lines.

13. The steam-assisted hydrocarbon recovery system of claim 10, wherein the steam characteristic is steam quality.

14. The steam-assisted hydrocarbon recovery system of claim 10, wherein the near-wellhead sensor module comprises a sensor configured to measure the total dissolved solids (TDS) of the steam.

* * * * *